United States Patent
Xi

(10) Patent No.: US 9,957,233 B1
(45) Date of Patent: May 1, 2018

(54) PROCESS FOR PREPARING SUBSTITUTED QUINOLIN-4-OL COMPOUNDS

(71) Applicants: Sunshine Lake Pharma Co., Ltd., Dongguan, Guangdong (CN); Calitor Sciences, LLC, Newbury Park, CA (US)

(72) Inventor: Ning Xi, Newbury Park, CA (US)

(73) Assignees: CALITOR SCIENCES, LLC, Newbury Park, CA (US); SUNSHIRE LAKE PHARMA CO., LTD., Dongguan, Guangdong (CN)

( * ) Notice: Subject to any disclaimer, the term of this patent is extended or adjusted under 35 U.S.C. 154(b) by 0 days. days.

(21) Appl. No.: 15/666,621

(22) Filed: Aug. 2, 2017

Related U.S. Application Data

(60) Provisional application No. 62/371,258, filed on Aug. 5, 2016.

(51) Int. Cl.
C07D 215/233 (2006.01)

(52) U.S. Cl.
CPC ................................ C07D 215/233 (2013.01)

(58) Field of Classification Search
CPC .................................................. C07D 215/233
See application file for complete search history.

(56) References Cited

U.S. PATENT DOCUMENTS

| | | | |
|---|---|---|---|
| 6,630,489 B1 | 10/2003 | Crawley | |
| 6,867,185 B2 | 3/2005 | Campbell et al. | |
| 6,995,174 B2 | 2/2006 | Wang et al. | |
| 7,091,214 B2 | 8/2006 | Hays et al. | |
| 7,253,286 B2 | 8/2007 | Funahashi et al. | |
| 7,449,479 B2 | 11/2008 | Wang et al. | |
| 7,511,157 B2 | 3/2009 | Bailey et al. | |
| 7,579,473 B2 | 8/2009 | Bannen et al. | |
| 7,598,382 B2 | 10/2009 | Hays et al. | |
| 7,691,850 B2 | 4/2010 | Miller et al. | |
| 7,696,242 B2 | 4/2010 | Bailey et al. | |
| 7,705,146 B2 | 4/2010 | Bailey et al. | |
| 7,776,857 B2 | 8/2010 | Cee et al. | |
| 7,973,164 B2 | 7/2011 | Jung et al. | |
| 8,017,779 B2 | 9/2011 | Merrill et al. | |
| 8,067,436 B2 | 11/2011 | Bannen et al. | |
| 8,124,602 B2 | 2/2012 | Breault et al. | |
| 8,178,532 B2 | 5/2012 | Bannen et al. | |
| 8,193,179 B2 | 6/2012 | Hubschwerlen et al. | |
| 8,232,294 B2 | 7/2012 | Xi | |
| 8,476,298 B2 | 7/2013 | Bannen et al. | |
| 8,497,284 B2 | 7/2013 | Bannen et al. | |
| 8,513,186 B2 | 8/2013 | Cottell et al. | |
| 8,557,816 B2 | 10/2013 | Geuns-Meyer et al. | |
| 8,557,984 B2 | 10/2013 | Bouillot et al. | |
| 8,809,267 B2 | 8/2014 | Cottell et al. | |
| 9,133,162 B2 | 9/2015 | Xi | |
| 9,174,947 B2 | 11/2015 | Bannen et al. | |
| 9,464,055 B2 * | 10/2016 | DeCorte et al. | C07D 215/44 |
| 9,604,963 B2 | 3/2017 | Bury et al. | |
| 2007/0259907 A1 | 11/2007 | Prince | |
| 2008/0004273 A1 | 1/2008 | Raeppel | |
| 2008/0161305 A1 | 7/2008 | Forsyth et al. | |
| 2009/0042910 A1 | 2/2009 | Jung | |
| 2012/0041024 A1 | 2/2012 | Charnley et al. | |
| 2012/0108577 A1 | 5/2012 | Breault et al. | |
| 2012/0208800 A1 | 8/2012 | Chung | |
| 2013/0150339 A1 | 6/2013 | Boezio et al. | |
| 2013/0225581 A1 | 8/2013 | Furuta et al. | |
| 2014/0256949 A1 | 9/2014 | Casillas et al. | |
| 2014/0275077 A1 | 9/2014 | Dandu et al. | |
| 2014/0336182 A1 | 11/2014 | Cee et al. | |
| 2015/0133436 A1 | 5/2015 | Chung | |
| 2015/0183802 A1 | 7/2015 | Chen et al. | |
| 2015/0209358 A1 | 7/2015 | Dandu et al. | |
| 2015/0210670 A1 | 7/2015 | Dandu et al. | |
| 2015/0284405 A1 | 10/2015 | Trzupek et al. | |
| 2015/0329498 A1 | 11/2015 | Romero et al. | |
| 2016/0060249 A1 | 3/2016 | Casillas et al. | |
| 2017/0050949 A1 | 2/2017 | Dandu et al. | |
| 2017/0096422 A1 | 4/2017 | Tsukamoto et al. | |
| 2017/0128437 A1 | 5/2017 | Bury et al. | |

FOREIGN PATENT DOCUMENTS

| | | |
|---|---|---|
| CN | 105111141 A | 9/2014 |
| WO | WO2007016610 A2 | 2/2007 |
| WO | Wo2008049047 A2 | 4/2008 |
| WO | WO2012136910 A1 | 10/2012 |
| WO | WO2012171487 A1 | 12/2012 |
| WO | WO20130180949 A1 | 12/2013 |
| WO | WO2014022128 A1 | 2/2014 |
| WO | 104211686 A | 12/2014 |
| WO | 2015/049629 * | 4/2015 |

(Continued)

OTHER PUBLICATIONS

Ilyas, CA148:561706, abstract only of J Labelled COmpounds and Radiopharmaceuticals, 2007, 50(5-6), 477-479. (Year: 2007).*

Jun Fan, Yang Dai, Jingwei Shao, Xia Peng, Chen Wang,Sufen Cao, Bin Zhao, Jing Ai, Meiyu Geng, Wenhu Duan, Design, synthesis and biological evaluation of pyrazolylaminoquinazoline derivatives as highly potent pan-fibroblast growth factor receptor inhibitors, Bioorganic & Medicinal Chemistry Letters, 2016, p. 2594-2599, vol. 26, Issue 11.

Pamela A et al., The Identification and Pharmacological Characterization of 6-(tert-Butylsulfonyl)-N-(5-fluoro-1H-Indazol-3-yl)quinolin-4-amine (GSK583), a Highly Potent and Selective Inhibitor of RIP2 Kinase, Journal of Medicinal Chemistry (2016), 59(10), p. 4867-4880.

Jose Augusto Berrocal et al., A CuI-Based Metallo-Supramolecular Gel-Like Material Built from a Library of Oligomeric Ligands Featuring Exotopic 1,10-Phenanthroline Units, European Journal of Organic Chemistry (2015), 2015(34), p. 7504-7510.

(Continued)

*Primary Examiner* — D Margaret M Seaman
(74) *Attorney, Agent, or Firm* — Kam W. Law; Squire Patton Boggs (US) LLP

(57) ABSTRACT

The invention relates to a process for preparing substituted quinolin-4-ol compounds useful for preparing protein tyrosine kinase (PTK) inhibitors which are useful in treating cancer.

16 Claims, No Drawings

(56) References Cited

FOREIGN PATENT DOCUMENTS

WO     WO2015049629 A1     4/2015
WO     WO2016055982 A1     4/2016

OTHER PUBLICATIONS

Davide Carta et al., Design, Synthesis, and Photophysical Properties of Pyrroloquinoline-Based Compounds Showing Strong Blue Fluorescence as Potential Dyes for Biomedical Applicat, ChemMedChem (2015), 10(11), p. 1846-1862.
Francesco Ferretti et al., Nitrogen ligands effects in the palladium-catalyzed carbonylation reaction of nitrobenzene to give N-methyl phenylcarbamate, Journal of Organometallic Chemistry (2014), 771, p. 59-67.
Samkele Nsumiwa et al., Structure—activity relationships for ferriprotoporphyrin IX association and b-hematin Inhibition by 4-aminoquinolines using experimental and ab initio methods, Bioorganic & Medicinal Chemistry (2013), 21(13), p. 3738-3748.
Matshawandile Tukulula et al., The design, synthesis, in silico ADME profiling, antiplasmodial and antimycobacterial evaluation of new arylamino quinoline derivatives, European Journal of Medicinal Chemistry (2012), 57, p. 259-267.
Laselo Lengyel et al., Highly efficient thermal cyclization reactions of alkylidene esters in continuous flow to give aromatic/heteroaromatic derivatives, Tetrahedron Letters (2012), 53(7), p. 738-743.
Jong Yeon Hwang et al., Synthesis and Evaluation of 7-Substituted 4-Aminoquinoline Analogues for Antimalarial Activity, Journal of Medicinal Chemistry (2011), 54(20), p. 7084-7093.
Francesco Ferretti et al., New Nonsymmetric Phenanthrolines as Very Effective Ligands in the Palladium-Catalyzed Carbonylation of Nitrobenzene, Organometallics (2010), 29(6), p. 1465-1471.
Tenzeela Ilyas et al., Microwave assisted synthesis of multiple labelled SR244870, a compound related to ferroquine (SSR97193), Journal of Labelled Compounds and Radiopharmaceuticals (2007), 50(5-6), p. 477-479.
Laurent Gomes et al., Novel pyrazole derivatives as potent inhibitors of type II topoisomerases. Part 1: Synthesis and preliminary SAR analysis, Bioorganic & Medicinal Chemistry Letters (2007), 17(10), p. 2723-2727.
Ryan A et al., 4,7-Dimethoxy-1,10-phenanthroline: An Excellent Ligand for the Cu-Catalyzed N-Arylation of Imidazoles, Organic Letters (2006), 8(13), p. 2779-2782.

* cited by examiner

PROCESS FOR PREPARING SUBSTITUTED QUINOLIN-4-OL COMPOUNDS

CROSS-REFERENCE TO RELATED APPLICATION

This application claims the benefit of U.S. Provisional Application No. 62/371,258, filed on Aug. 5, 2016, which is hereby incorporated by reference in its entirety.

FIELD OF THE INVENTION

This invention relates to a process for a large scale preparation of substituted quinolin-4-ol compounds, which are intermediates for preparing protein tyrosine kinase (PTK) inhibitors useful for treating cancer.

BACKGROUND OF THE INVENTION

Substituted quinolin-4-ol compounds are intermediates for preparing protein tyrosine kinase (PTK) inhibitors useful for treating cancer. Protein tyrosine kinases (PTK) are a subclass of protein kinases and play a key role in the regulation of cell proliferation, differentiation, metabolism, migration, and survival. They are further classified as receptor tyrosine kinases (e.g. Axl, VEGFR, c-Met (HGFR), Ron, EGFR, PDGFR, and FGFR) or non-receptor (e.g. c-src and bcr-abl) kinases. Receptor tyrosine kinases are transmembrane proteins that possess an extracellular binding domain for growth factors, a transmembrane domain, and an intracellular portion that functions as a kinase to phosphorylate a specific tyrosine residue in downstream proteins. Abnormal expression or aberrant activity of protein kinases has been directly implicated in the pathogenesis of many human cancers.

WO 2012/118632, WO 2013/180949 and WO 2014/022128 disclosed methods for preparing of the compound of the Formula (I) in small scale. The specific methods are shown below:

1. The method disclosed in WO 2012/118632 is shown in scheme (A):

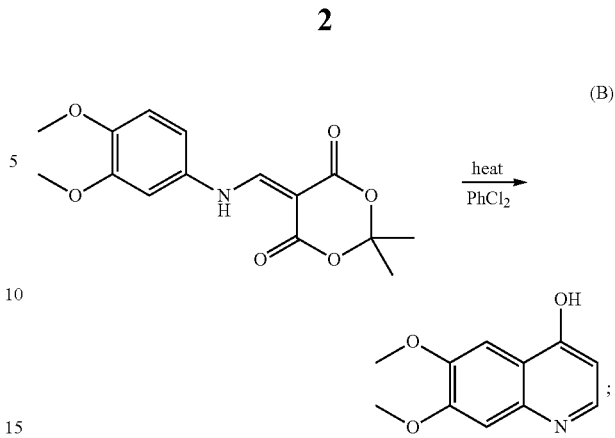

(A)

2. The method disclosed in WO 2013/180949 is shown in scheme (B):

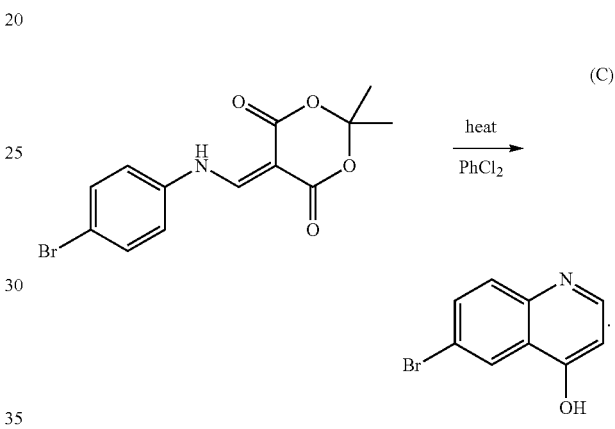

(B)

3. The method disclosed in WO 2014/022128 is shown in scheme (C):

(C)

WO 2013/086229 also disclosed a method for preparing the compound of the Formula (I) under microwave conditions as shown in the scheme below:

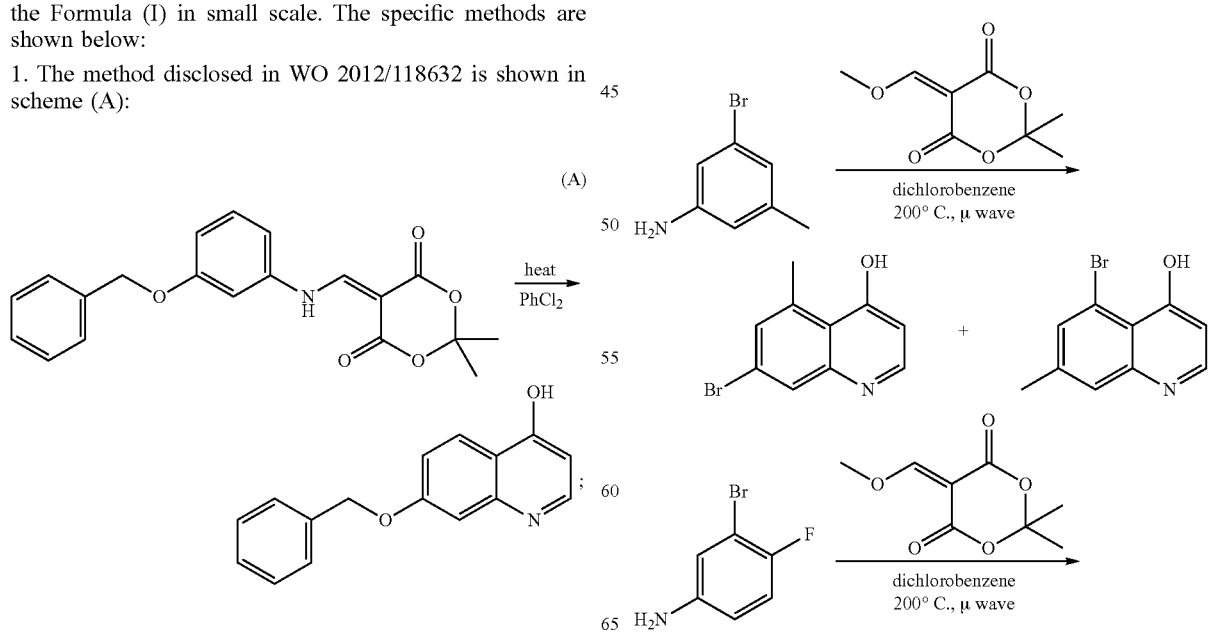

-continued

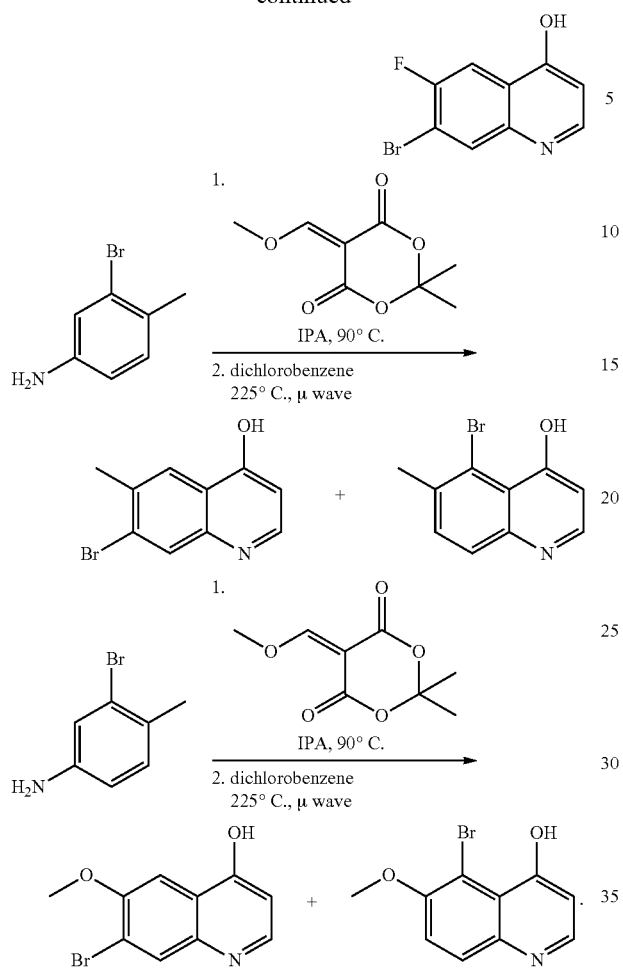

The above mentioned processes were all carried out at gram scales and are not suitable for GMP-compliance kilogram scale production. Especially, the procedure described in the patent application WO 2013/086229 is carried out using microwave radiation method, which is not intend to be used on plant production scale.

Substituted quinolin-4-ol compounds have been used as the common intermediates for manufacturing various protein tyrosine kinase (PTK) inhibitors, therefore there is a need in the art for a large scale preparation method, which is simple, convenient, economical and industrially viable, for preparing substituted quinolin-4-ol compounds.

The object of the present invention provides a practical process for preparing and purifying the compound of Formula (I) in multi-kilogram scale, avoiding excessive formation of byproducts during the reaction, improving the yield and simplifying the purification process.

SUMMARY OF THE INVENTION

In one aspect provided herein is a process for preparing the compound of Formula (I),

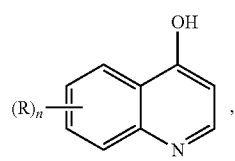

wherein:

each R is independently F, Cl, Br, I, CN, $(C_1-C_6)$alkyl, $OR^a$, or $NR^bR^c$;

n is 0, 1, 2, 3, or 4;

each of $R^a$, $R^b$ and $R^c$ is independently H, $(C_1-C_6)$alkyl, $(C_3-C_6)$cycloalkyl, —$(C_1-C_4)$alkylene-$(C_3-C_6)$cycloalkyl, 3-6 membered heterocyclyl, —$(C_1-C_4)$alkylene-(3-6 membered heterocyclyl), $(C_6-C_{10})$aryl, —$(C_1-C_4)$alkylene-$(C_6-C_{10})$aryl, 5-10 membered heteroaryl, or —$(C_1-C_4)$alkylene-(5-10 membered heteroaryl), wherein each of the $(C_1-C_6)$ alkyl, $(C_3-C_6)$cycloalkyl, —$(C_1-C_4)$alkylene-$(C_3-C_6)$ cycloalkyl, 3-6 membered heterocyclyl, —$(C_1-C_4)$alkylene-(3-6 membered heterocyclyl), $(C_6-C_{10})$aryl, —$(C_1-C_4)$ alkylene-$(C_6-C_{10})$aryl, 5-10 membered heteroaryl and —$(C_1-C_4)$alkylene-(5-10 membered heteroaryl) is optionally substituted with 1, 2, 3, or 4 substitutents independently selected from F, Cl, CN, $N_3$, OH, $(C_1-C_6)$alkyl, $(C_1-C_6)$ haloalkyl, and $(C_1-C_6)$alkoxy;

and wherein the compound of Formula (I) is not one of the following compounds:

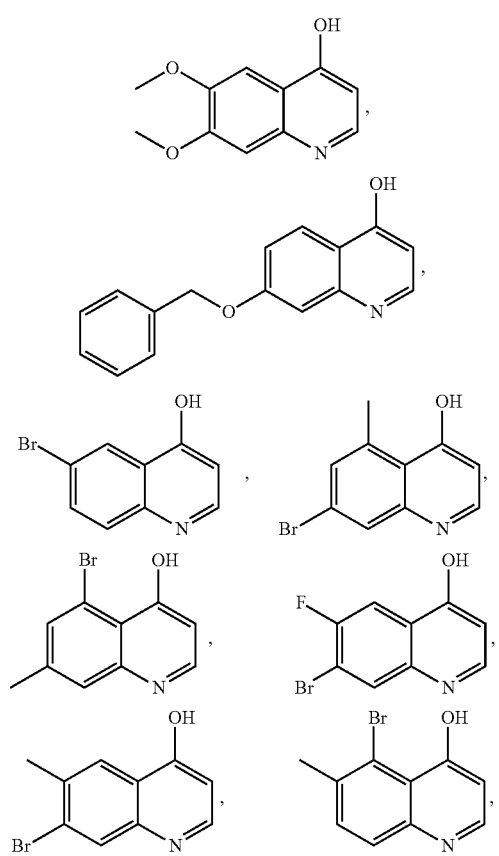

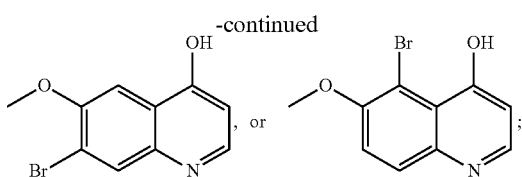

the process comprising:
contacting the compound of Formula (II)

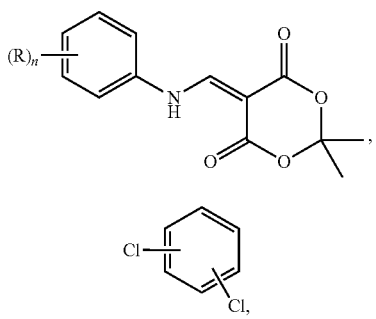

with a dichlorobenzene of Formula (III) to obtain a reaction mixture containing the compound of Formula (I);
wherein the dichlorobenzene of Formula (III) is

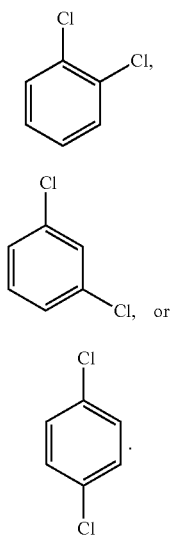

In one embodiment, each R is independently F, I, CN, methyl, ethyl, n-propyl, propyl, n-butyl, i-butyl, t-butyl, $OR^a$, or $NR^bR^c$.

In another embodiment, each of $R^a$, $R^b$ and $R^c$ is independently H, $(C_1-C_4)$alkyl, $(C_5-C_6)$cycloalkyl, $-(C_1-C_2)$alkylene-$(C_5-C_6)$cycloalkyl, 5-6 membered heterocyclyl, $-(C_1-C_2)$alkylene-(5-6 membered heterocyclyl), phenyl, $-(C_1-C_2)$alkylene-phenyl, or 5-6 membered heteroaryl, wherein each of the $(C_1-C_4)$alkyl, $(C_5-C_6)$cycloalkyl, $-(C_1-C_2)$alkylene-$(C_5-C_6)$cycloalkyl, 5-6 membered heterocyclyl, $-(C_1-C_2)$alkylene-(5-6 membered heterocyclyl), phenyl, $-(C_1-C_2)$alkylene-phenyl, and 5-6 membered heteroaryl, is optionally substituted with 1, 2, 3, or 4 substitutents independently selected from F, Cl, CN, $N_3$, OH, $(C_1-C_3)$alkyl, and $(C_1-C_3)$alkoxy.

In one embodiment, each of $R^a$, $R^b$ and $R^c$ is independently H, methyl, ethyl, n-propyl, i-propyl, n-butyl, i-butyl, or t-butyl.

In another embodiment, the compound of Formula (I) is compound (Ia),

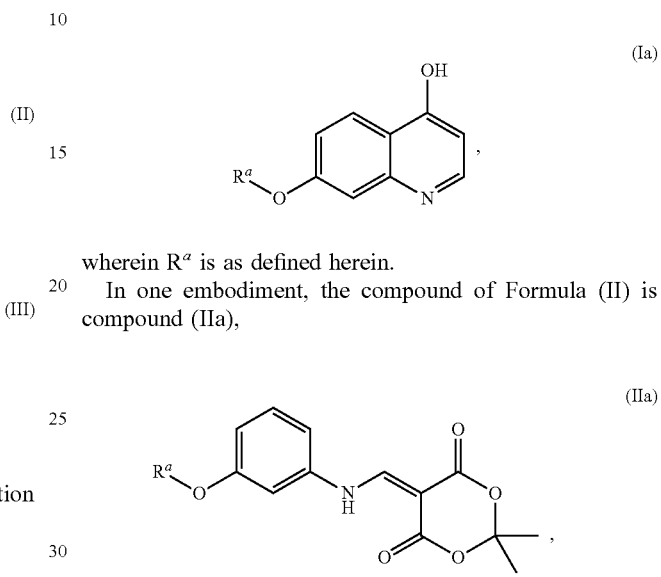

wherein $R^a$ is as defined herein.

In one embodiment, the compound of Formula (II) is compound (IIa),

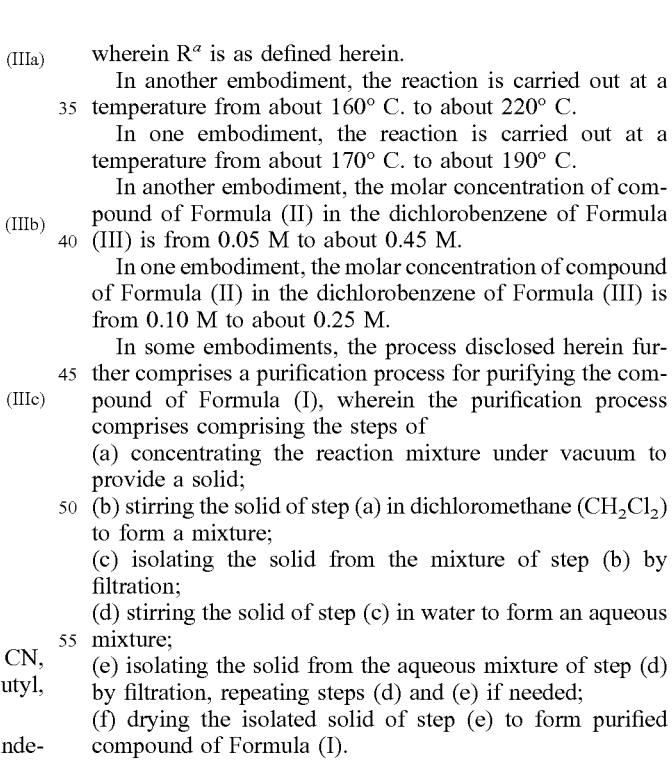

wherein $R^a$ is as defined herein.

In another embodiment, the reaction is carried out at a temperature from about 160° C. to about 220° C.

In one embodiment, the reaction is carried out at a temperature from about 170° C. to about 190° C.

In another embodiment, the molar concentration of compound of Formula (II) in the dichlorobenzene of Formula (III) is from 0.05 M to about 0.45 M.

In one embodiment, the molar concentration of compound of Formula (II) in the dichlorobenzene of Formula (III) is from 0.10 M to about 0.25 M.

In some embodiments, the process disclosed herein further comprises a purification process for purifying the compound of Formula (I), wherein the purification process comprises comprising the steps of (a) concentrating the reaction mixture under vacuum to provide a solid;
(b) stirring the solid of step (a) in dichloromethane ($CH_2Cl_2$) to form a mixture;
(c) isolating the solid from the mixture of step (b) by filtration;
(d) stirring the solid of step (c) in water to form an aqueous mixture;
(e) isolating the solid from the aqueous mixture of step (d) by filtration, repeating steps (d) and (e) if needed;
(f) drying the isolated solid of step (e) to form purified compound of Formula (I).

In one embodiment, a ratio of the weight (in gram) of the solid obtained in step (a) to the volume (in mL) of $CH_2Cl_2$ used in step (b) is from about 0.4 to about 0.8.

In another embodiment, a ratio of the weight (in gram) of the solid obtained in step (a) to the volume (in mL) of $CH_2Cl_2$ used in step (b) is from about 0.5 to about 0.7.

In one embodiment, the mixture in step (b) is stirred at 45° C. for 2 hours.

In another embodiment, the aqueous mixture in step (d) is stirred at 100° C. for 2 hours.

In one embodiment, the filtration in step (e) is carried out at a temperature from about 25° C. to about 60° C.

The compound of Formula (II) can be prepared as described in WO 2012/118632, the entire contents of which is incorporated by reference.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

Unless defined otherwise, all technical and scientific terms used herein have the same meaning as is commonly understood by one of skill in the art to which this invention belongs. All patents and publications referred to herein are incorporated by reference.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry," by Michael B. Smith and Jerry March, John Wiley & Sons, New York: 2007, all of which are incorporated by reference in their entireties.

The disclosure described herein contains different aspects and embodiments, and each aspect and embodiment is non-limiting in regard to the scope of the disclosure. The terms "aspects" and "embodiments" are meant to be non-limiting regardless of where the terms "aspect" or "embodiment" appears in this specification. The transitional term "comprising" as used herein, which is synonymous with "including," "containing," or "characterized by," is inclusive or open-ended and does not exclude additional, un-recited elements.

The "about" disclosed herein refers to the value of each number may differ by 0.5%, 1%, 1.5%, 2%, or 2.5%. In some embodiments, the value of each number may differ by 1%. In other embodiments, the value of each number may differ by 1.5%. In other embodiments, the value of each number may differ by 2%.

In the present context, all numbers disclosed herein are approximate values, and the value of each number may differ by 1%, 2%, 5%, 7%, 8%, 10% and so on. Therefore, whenever a number having a value N is disclosed, any number having the value N+/−1%, N+/−2%, N+/−3%, N+/−5%, N+/−7%, N+/−8%, or N+/−10% is specifically disclosed, wherein "+/−" refers to plus or minus. Whenever a numerical range with a lower limit, DL and an upper limit, DL, is disclosed, any number falling within the range is specifically disclosed.

After the reaction proceeds to a certain extent in the present invention, such as the raw material is consumed more than 70%, more than 80%, more than 90%, more than 95%, or completely by monitoring, the reaction mixture is worked up, such as cooled, collected, drawn, filtered, separated, purified or a combination thereof. The reaction can be monitored by conventional method such as thin-layer chromatography (TLC), high performance liquid chromatography (HPLC), gas chromatography (GC), and the like. The reaction mixture can be worked up by conventional method, for example, the crude product can be collected by concentrating the reaction mixture through vacuum evaporation or conventional distillation and which is used directly in the next operation; or the crude product can be obtained by filtration of the reaction mixture and which is used directly in the next operation; or the crude product can be get by pouring the supernatant liquid of the reaction mixture after standing for a while and which is used directly in the next operation. Or the reaction mixture can be purified by suitable methods such as extraction, distillation, crystallization, column chromatography, washing, trituration with suitable solvents or a combination thereof.

Each process and each step in the reaction sequence disclosed herein are proceed under certain temperature conditions. Any suitable temperature for the dropping process or the reaction are included in the invention. Additionally, the field of many similar changes, equivalent replacement, or equivalent temperature and temperature range described in the invention, are considered to be within the scope of the invention. The invention provides the preferred temperature or temperature range of dripping process, and the preferred temperature of the reaction.

The solvents used in each reaction step are not particularly restricted. Any solvent which can dissolve the starting material in a certain extent and does not inhibit the reaction is included in the invention. Additionally, the field of many similar changes, equivalent replacement, or equivalent solvents described in the invention, solvents combination and the proportions of solvent combination are considered to be within the scope of the invention. The invention provides the preferred solvents of each reaction steps.

The "room temperature" disclosed herein refers to the temperature from about 10° C. to about 40° C. In some embodiments, the room temperature is from about 20° C. to about 30° C. In other embodiments, the room temperature is about 20° C., about 22.5° C., about 25° C. or about 27.5° C., and so on.

The term "base" is inclusive of an organic or inorganic base. Some non-limiting examples of the organic base include triethylamine, trimethylamine, N,N-diisopropylethylamine, N-methylmorpholine, N-methylpiperidine, or pyridine. Some non-limiting examples of the inorganic base include the alkali metal or alkaline earth metal hydroxide, alkali metal or alkaline earth metal alkoxides, alkali metal or alkaline earth metal carbonate or bicarbonate or phosphate or hydrogen phosphate, or ammonia. In some embodiments, the base disclosed herein is an organic base. In some embodiments, the base disclosed herein is an inorganic base. In some embodiments, the base disclosed herein is triethylamine, trimethylamine, N,N-diisopropylethylamine, N-methylmorpholine, N-methylpiperidine, pyridine, sodium hydroxide, potassium hydroxide, potassium tert-butoxide, potassium carbonate, sodium carbonate, potassium bicarbonate, sodium dicarbonate, sodium phosphate, potassium phosphate, disodium hydrogen phosphate, dipotassium hydrogen phosphate or a combination thereof. In some embodiments, the base disclosed herein is sodium hydroxide, potassium hydroxide, potassium tert-butoxide, potassium carbonate, sodium carbonate, potassium bicarbonate, sodium dicarbonate, sodium phosphate, potassium phosphate, disodium hydrogen phosphate, or dipotassium hydrogen phosphate.

As described herein, the phrase "optionally substituted" is used interchangeably with the phrase "substituted or unsubstituted". In general, the term "substituted" refers to the replacement of one or more hydrogen radicals in a given structure with the radical of a specified substituent. The term "optional" or "optionally" means that the subsequently described event or circumstance may but need not occur, and that the description includes instances where the event or circumstance occurs and instances in which it does not. Unless otherwise indicated, an optionally substituted group may have a substituent at each substitutable position of the group. When more than one position in a given structure can be substituted with more than one substituent selected from a specified group, the substituent may be either the same or different at each position.

The term "alkyl" or "alkyl group" refers to a saturated linear or branched-chain monovalent hydrocarbon radical of 1 to 20 carbon atoms, wherein the alkyl radical may be optionally substituted independently with one or more substituents described below. Unless otherwise specified, the alkyl group contains 1-20 carbon atoms. In some embodiments, the alkyl group contains 1-12 carbon atoms. In other embodiments, the alkyl group contains 1-10 carbon atoms. In other embodiments, the alkyl group contains 1-8 carbon atoms. In other embodiments, the alkyl group contains 1-6 carbon atoms. In still other embodiments, the alkyl group contains 1-4 carbon atoms, and in yet other embodiments, the alkyl group contains 1-3 carbon atoms.

Some non-limiting examples of the alkyl group include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, the alkylene group contains 1-6 carbon atoms. In some embodiments, the alkylene group contains 1-4 carbon atoms. In other embodiments, the alkylene group contains 1-2 carbon atoms. Some non-limiting examples of the alkylene group include methylene (—CH$_2$—), ethylidene (—CH$_2$CH$_2$—), isopropylidene (—CH(CH$_3$)CH$_2$—), and the like.

The term "haloalkyl", "haloalkenyl" or "haloalkoxy" refers to alkyl, alkenyl, or alkoxy, as the case may be, substituted with one or more halogen atoms. Some non-limiting examples of the above groups include trifluoromethyl (—CF$_3$), trifluoromethoxy (—OCF$_3$), and the like.

The term "cycloalkyl" refers to a monovalent or multivalent saturated ring having 3 to 12 carbon atoms as a monocyclic, bicyclic, or tricyclic ring system. A bicyclic ring system includes a spiro bicyclyl or a fused bicyclyl. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms, and in yet other embodiments, the cycloalkyl group contains 5 to 6 carbon atoms. Some non-limiting examples of the cycloalkyl group include cyclopropyl, cyclobutyl, cyclopentyl, cyclohexyl, cycloheptyl, and the like. The cycloalkyl group is optionally substituted independently with one or more substituents described herein.

The term "heterocycle", "heterocyclyl", or "heterocyclic ring" as used interchangeably herein refers to a saturated or partially unsaturated, but not aromatic monocyclic, bicyclic or tricyclic ring containing 3-12 ring atoms of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of the heterocyclyl include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl, diazepinyl, thiazepinyl, indolinyl, 1,2,3,4-tetrahydroisoquinolinyl, 1,3-benzodioxolyl, 2-oxa-5-azabicyclo[2.2.1]hept-5-yl. Some non-limiting examples of the heterocyclyl wherein —CH$_2$— group is replaced by —C(=O)— moiety are 2-oxopyrrolidinyl, oxo-1,3-thiazolidinyl, 2-piperidinonyl, and 3,5-dioxopiperidinyl. Some non-limiting examples of the heterocyclyl wherein the ring sulfur atom is oxidized are sulfolanyl and 1,1-dioxo-thiomorpholinyl. The heterocyclyl group may be optionally substituted with one or more substituents described herein.

In another embodiments, heterocyclyl may be 3-6 membered heterocyclyl, which refers to a saturated or partially unsaturated monocyclic ring containing 3-6 ring atoms, of which at least one ring atom is selected from nitrogen, sulfur and oxygen, and of which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of the 3-6 membered heterocyclyl include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, and dithianyl. Some non-limiting examples of the heterocyclyl wherein —CH$_2$— group is replaced by —C(=O)— moiety are 2-oxopyrrolidinyl, oxo-1,3-thiazolidinyl, 2-piperidinonyl, and 3,5-dioxopiperidinyl. Some non-limiting examples of the heterocyclyl wherein the ring sulfur atom is oxidized are sulfolanyl and 1,1-dioxo-thiomorpholinyl. The 3-6 membered heterocyclyl group may be optionally substituted with one or more substituents described herein.

In another embodiments, heterocyclyl may be 5-6 membered heterocyclyl, which refers to a saturated or partially unsaturated monocyclic ring containing 5-6 ring atoms, of which at least one ring atom is selected from nitrogen, sulfur and oxygen, and of which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of the 5-6 membered heterocyclyl include pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, and dithianyl. Some non-limiting examples of the heterocyclyl wherein —CH$_2$— group is replaced by —C(=O)— moiety are 2-oxopyrrolidinyl, oxo-1,3-thiazolidinyl, 2-piperidinonyl, and 3,5-dioxopiperidinyl. Some non-limiting examples of the heterocyclyl wherein the ring sulfur atom is oxidized are sulfolanyl and 1,1-dioxo-thiomorpholinyl. The 5-6 membered heterocyclyl group may be optionally substituted with one or more substituents described herein.

In another embodiments, heterocyclyl may be a 5-membered heterocyclyl, which refers to a saturated or partially unsaturated monocyclic ring containing 5 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of the 5-membered heterocyclyl include pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, and dithiolanyl. Some non-limiting examples of the heterocyclyl wherein —CH$_2$— group is replaced by —C(=O)— moiety are 2-oxopyrrolidinyl and oxo-1,3-thiazolidinyl. Some non-limiting examples of the heterocyclyl wherein the ring sulfur atom is oxidized is sulfolanyl. The 5-membered heterocyclyl group may be optionally substituted with one or more substituents described herein.

In still another embodiments, heterocyclyl may be a 6-membered heterocyclyl, which refers to a saturated or partially unsaturated monocyclic ring containing 6 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of the 6-membered heterocyclyl include tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, and dithianyl. Some non-limiting examples of the heterocyclyl wherein —CH$_2$— group is replaced by —C(=O)— moiety are 2-piperidinonyl, and 3,5-dioxopiperidinyl. A non-limiting examples of the heterocyclyl wherein the ring sulfur atom is oxidized is 1,1-dioxothiomorpholinyl. The 6-membered heterocyclyl group is optionally substituted with one or more substituents described herein.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to Fluoro (F), Chloro (Cl), Bromo (Br), or Iodo (I).

The term "aryl" used alone or as part of a larger moiety as in "aralkyl", "aralkoxy" or "aryloxyalkyl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic, wherein each ring in the system contains 3 to 7 ring members and that has one or more points of attachment to the rest of the molecule. The term "aryl" may be used interchangeably with the term "aryl ring" or "aromatic." Some non-limiting examples of the aryl ring would include phenyl, naphthyl, and anthracenyl. The aryl radical is optionally substituted independently with one or more substituents described herein.

The term "heteroaryl" used alone or as part of a larger moiety as in "heteroaralkyl" or "heteroarylalkoxy" refers to monocyclic, bicyclic, and tricyclic ring systems having a total of 5 to 14 ring members, preferably, 5 to 12 ring members, and more preferably 5 to 10 ring members, wherein at least one ring in the system is aromatic, at least one ring in the system contains one or more heteroatoms, wherein each ring in the system contains 5 to 7 ring members and that has one or more points of attachment to the rest of the molecule. In some embodiments, heteroaryl may be a 5-10 membered heteroaryl comprises 1, 2, 3 or 4 heteroatoms independently selected from O, S and N. In other embodiments, heteroaryl may be a 5-6 membered heteroaryl comprises 1, 2, 3 or 4 heteroatoms independently selected from O, S and N. In still other embodiments, heteroaryl may be a 5-membered heteroaryl comprises 1, 2, 3 or 4 heteroatoms independently selected from O, S and N. In still other embodiments, heteroaryl may be a 6-membered heteroaryl comprises 1, 2, 3 or 4 heteroatoms independently selected from O, S and N. The term "heteroaryl" may be used interchangeably with the term "heteroaryl ring" or the term "heteroaromatic". The heteroaryl radicals are optionally substituted independently with one or more substituents described herein.

Some non-limiting examples of the heteroaryl ring include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl and 2H-tetrazolyl), triazolyl (e.g., 2-triazolyl, 5-triazolyl, 4H-1,2,4-triazolyl, 1H-1,2,4-triazolyl, and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-triazolyl, 1,2,4-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "alkylamino" embraces "N-alkylamino" and "N,N-dialkylamino" where amino groups are independently substituted with one alkyl radical or with two alkyl radicals, respectively. Some non-limiting examples of alkylamino radicals are "lower alkylamino" radicals having one or two alkyl radicals of one to six carbon atoms, attached to a nitrogen atom. Suitable alkylamino radicals may be mono or dialkylamino such as N-methylamino, N-ethylamino, N, N-dimethylamino, N, N-diethylamino and the like.

The term "alkoxy" refers to an alkyl group, as previously defined, attached to the principal carbon atom through an oxygen atom. Unless otherwise specified, the alkoxy group contains 1-20 carbon atoms. In some embodiments, the alkoxy group contains 1-10 carbon atoms. In other embodiments, the alkoxy group contains 1-8 carbon atoms. In still other embodiments, the alkoxy group contains 1-6 carbon atoms, and in yet other embodiments, the alkoxy group contains 1-4 carbon atoms. In further embodiments, the alkoxy group contains 1-3 carbon atoms.

Some non-limiting examples of the alkoxy group include methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "n membered" where n is an integer typically describes the number of ring-forming atoms in a moiety where the number of ring-forming atoms is n. For example, piperidinyl is an example of a 6 membered heterocycloalkyl and 1,2,3,4-tetrahydro naphthalenyl is an example of a 10 membered carbocyclyl group.

The term "unsaturated" refers to a moiety having one or more units of unsaturation.

The term "comprising" is meant to be open ended, including the indicated component but not excluding other elements.

As described herein, a bond drawn from a substituent to the center of one ring within a ring system (as shown below) represents substitution of the substituent at any substitutable position on the ring to which it is attached. For example, Structure a represents possible substitution in any of the positions on the A ring shown in Structure b-1, b-2, b-3 and b-4.

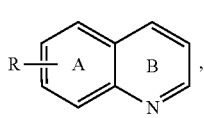

Structure b

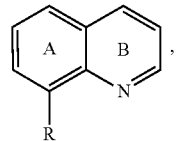

Structure b-1

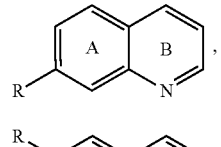

Structure c-1

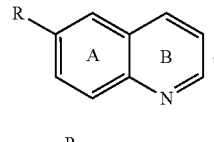

Structure c-2

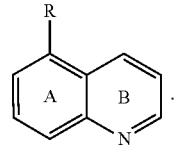

Structure c-2

DESCRIPTION OF THE PROCESS OF THE INVENTION

One aspect provides a process for preparing the compound of Formula (I),

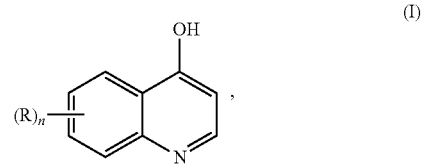

wherein:

each R is independently F, Cl, Br, I, CN, (C$_1$-C$_6$)alkyl, OR$^a$, or NR$^b$R$^c$;

n is 0, 1, 2, 3, or 4;

each of R$^a$, R$^b$ and R$^c$ is independently H, (C$_1$-C$_6$)alkyl, (C$_3$-C$_6$)cycloalkyl, —(C$_1$-C$_4$)alkylene-(C$_3$-C$_6$)cycloalkyl, 3-6 membered heterocyclyl, —(C$_1$-C$_4$)alkylene-(3-6 membered heterocyclyl), (C$_6$-C$_{10}$)aryl, —(C$_1$-C$_4$)alkylene-(C$_6$-C$_{10}$)aryl, 5-10 membered heteroaryl, or —(C$_1$-C$_4$)alkylene-(5-10 membered heteroaryl), wherein each of the (C$_1$-C$_6$) alkyl, (C$_3$-C$_6$)cycloalkyl, —(C$_1$-C$_4$)alkylene-(C$_3$-C$_6$) cycloalkyl, 3-6 membered heterocyclyl, —(C$_1$-C$_4$)alkylene-(3-6 membered heterocyclyl), (C$_6$-C$_{10}$)aryl, —(C$_1$-C$_4$) alkylene-(C$_6$-C$_{10}$)aryl, 5-10 membered heteroaryl and —(C$_1$-C$_4$)alkylene-(5-10 membered heteroaryl) is optionally substituted with 1, 2, 3, or 4 substitutents independently selected from F, Cl, CN, N$_3$, OH, (C$_1$-C$_6$)alkyl, (C$_1$-C$_6$) haloalkyl, and (C$_1$-C$_6$)alkoxy;

and wherein the compound of Formula (I) is not one of the following compounds:

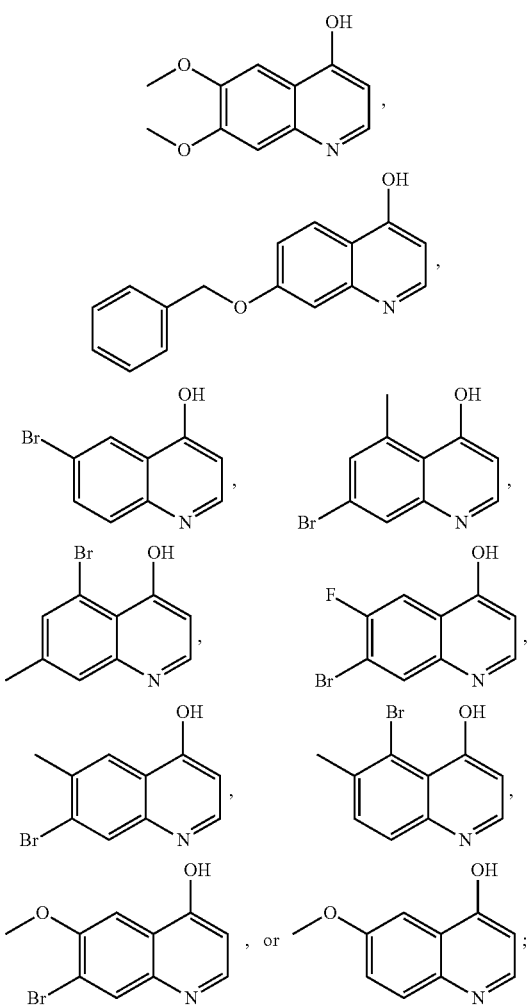

the process comprising:
contacting the compound of Formula (II)

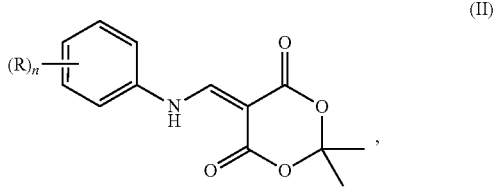

with a dichlorobenzene of Formula (III) to obtain a reaction mixture containing the compound of Formula (I);

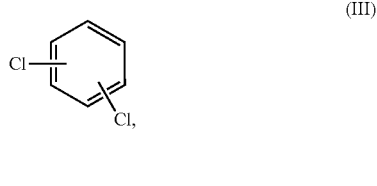

wherein the dichlorobenzene of Formula (III) is

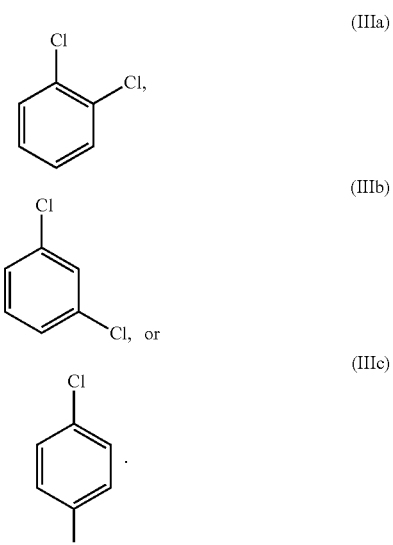

In one embodiment, each R is independently F, I, CN, methyl, ethyl, n-propyl, propyl, n-butyl, i-butyl, t-butyl, OR$^a$, or NR$^b$R$^c$.

In another embodiment, each of R$^a$, R$^b$ and R$^c$ is independently H, (C$_1$-C$_4$)alkyl, (C$_5$-C$_6$)cycloalkyl, —(C$_1$-C$_2$)alkylene-(C$_5$-C$_6$)cycloalkyl, 5-6 membered heterocyclyl, —(C$_1$-C$_2$)alkylene-(5-6 membered heterocyclyl), phenyl, —(C$_1$-C$_2$)alkylene-phenyl, or 5-6 membered heteroaryl, wherein each of the (C$_1$-C$_4$)alkyl, (C$_5$-C$_6$)cycloalkyl, —(C$_1$-C$_2$)alkylene-(C$_5$-C$_6$)cycloalkyl, 5-6 membered heterocyclyl, —(C$_1$-C$_2$)alkylene-(5-6 membered heterocyclyl), phenyl, —(C$_1$-C$_2$)alkylene-phenyl, and 5-6 membered heteroaryl, is optionally substituted with 1, 2, 3, or 4 substitutents independently selected from F, Cl, CN, N$_3$, OH, (C$_1$-C$_3$)alkyl, and (C$_1$-C$_3$)alkoxy.

In one embodiment, each of R$^a$, R$^b$ and R$^c$ is independently H, methyl, ethyl, n-propyl, i-propyl, n-butyl, i-butyl, or t-butyl.

In another embodiment, the compound of Formula (I) is compound (Ia),

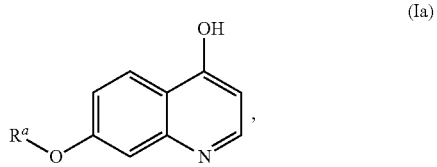

wherein R$^a$ is as defined herein.

In one embodiment, the compound of Formula (II) is compound (IIa),

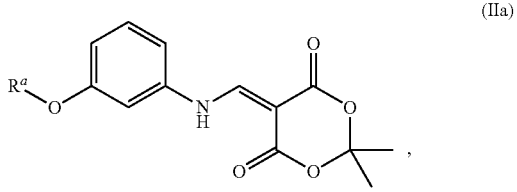

wherein R$^a$ is as defined herein.

In another embodiment, the reaction is carried out at a temperature from about 160° C. to about 220° C.

In one embodiment, the reaction is carried out at a temperature from about 170° C. to about 190° C.

In another embodiment, the molar concentration of compound of Formula (II) in the dichlorobenzene of Formula (III) is from about 0.05 M to about 0.45 M.

In one embodiment, the molar concentration of compound of Formula (II) in the dichlorobenzene of Formula (III) is from about 0.10 M to about 0.25 M.

In some embodiments, the process disclosed herein further comprises a purification process for purifying the compound of Formula (I), wherein the purification process comprises the steps of
(a) concentrating the reaction mixture under vacuum to provide a solid;
(b) washing the said solid of step (a) with dichloromethane;
(c) isolating the resulted solid from step (b) by filtration;
(d) washing the solid of step (c) with water, repeating the washing process if needed;
(e) isolating the purified solid of compound of formula (I) by filtration;
(f) drying the isolated solid of step (e).

In one embodiment, a ratio of the weight (in gram) of the solid obtained in step (a) to the volume (in mL) of $CH_2Cl_2$ used in step (b) is from about 0.4 to about 0.8.

In another embodiment, a ratio of the weight (in gram) of the solid obtained in step (a) to the volume (in mL) of $CH_2Cl_2$ used in step (b) is from about 0.5 to about 0.7.

In one embodiment, the mixture in step (b) is stirred at 45° C. for 2 hours.

In another embodiment, the mixture of the solid of step (e) with water is stirred at 100° C. for 2 hours.

In one embodiment, the filtration in step (e) is carried out at a temperature from about 25° C. to about 60° C.

The compound of Formula (II) can be prepared as described in WO 2012/118632, the entire contents of which is incorporated by reference.

General Synthetic Procedures

In order to illustrate the invention, the following examples are included. However, it is to be understood that these examples do not limit the invention and are only meant to suggest a method of practicing the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tainjin YuYu Fine Chemical Ltd., Qingdao Tenglong Reagent Chemical Ltd., and Qingdao Ocean Chemical Factory.

Glassware used in the reactions set forth below was oven dried and/or heat dried.

$^1$H NMR spectra were recorded with a Bruker 400 MHz spectrometer or a Bruker 600 MHz spectrometer at ambient temperature. $^1$H NMR spectra were obtained as $CDCl_3$, DMSO-$d_6$, $CD_3OD$ or acetone-$d_6$ solutions (reported in ppm), using TMS (0 ppm) or chloroform (7.26 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants (J), when given, are reported in Hertz (Hz).

Low-resolution mass spectral (MS) data were generally determined on an Agilent 6120 Quadrupole HPLC-MS (Zorbax SB-C18, 2.1×30 mm, 3.5 micron, 6 minutes run, 0.6 mL/min flow rate, 5% to 95% (0.1% formic acid in $CH_3CN$) in (0.1% formic acid in $H_2O$)) with UV detection at 210 nm/254 nm and electrospray ionization mode (ESI).

Purities of compounds were assessed by Agilent 1260 Pre-HPLC or Calesep Pump 250 Pre-HPLC (Column NOVASEP 50/80 mm DAC) with UV detection at 210 nm/254 nm.

The following abbreviations are used throughout the specification:

$BiCl_3$ bismuth chloride $CH_2Cl_2$, DCM dichloromethane

DMF N,N-dimethylformamide

DMSO dimethyl sulfoxide eq, eq. equivalent h hour $H_2SO_4$ sulfuric acid

HPLC High Performance Liquid Chromatography

L Liter m mass

M molar mass o-DCB ortho-dichlorobenzene

Pre-HPLC Preparative High Performance Liquid Chromatography

TsOH p-toluenesulfonic acid

T temperature t time

V Volume $ZnCl_2$ zinc chloride

The process of the invention is shown in Scheme 1. Unless otherwise indicated, R and n carry the definitions set forth above in connection with Formula (I).

Scheme 1

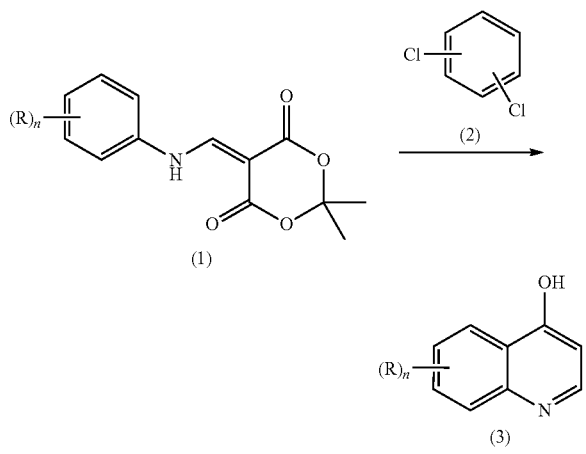

Compound (1) is reacted in dichlorobenzene (2) under heating conditions to give compound (3).

EXAMPLES

Example 1 7-methoxyquinolin-4-ol

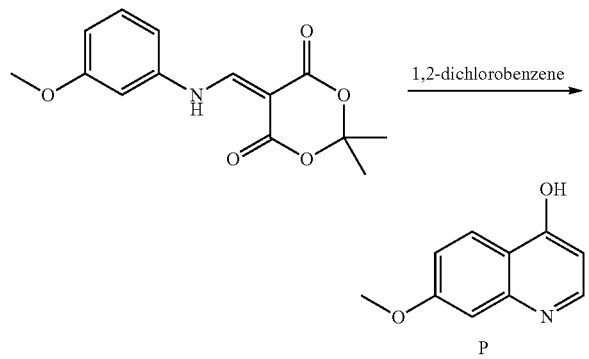

To a stirred 1,2-dichlorobenzene (4 L) in a four-neck bottle (5 L) was added 5-(((3-methoxyphenyl)amino)methylene)-2,2-dimethyl-1,3-dioxane-4,6-dione (110.8 g, 400 mmol). The reaction was heated to 180° C. and continued to stir for 3 hours. Upon the completion, the crude reaction mixture was concentrated in vacuo until the volume of 1,2-dichlorobenzene was reduced to approximately 3.5 L. The residue was left standing overnight, and filtered to afford the crude product as a yellow solid. The crude product was stirred with $CH_2Cl_2$ ($m_{crude\,product}/V_{CH2Cl2}$=0.5 (g/mL)) at 45° C. for 2 hours, and then filtrated to wash off part of the remaining solvent (1,2-dichlorobenzene) and a portion of impurities. This washing process can be repeated when needed (usually repeated twice). The solid was dried in vacuo and then stirred with water ($m_{solid}/V_{H2O}$=0.45 (g/mL)) at 100° C. for 2 hours. The mixture was cooled to from about 30° C. to about 50° C., then filtered to remove water. This process can be repeated if needed (usually repeated once). The collected solid was dried in vacuo to give the title compound as a pale yellow solid (36.2 g, Yield: 51.8%, HPLC: 96.4%).

MS (ESI, pos. ion) m/z: 176.1 [M+H]$^+$;

$^1$H NMR (400 MHz, DMSO-d$_6$) δ (ppm): 11.54 (s, 1H), 7.98 (d, J=9.5 Hz, 1H), 7.85-7.76 (m, 1H), 6.95-6.86 (m, 2H), 5.94 (d, J=7.4 Hz, 1H), 3.84 (s, 3H).

The Optimization of the Reaction Conditions:
1. The Effects of the Solvents, Catalysts and Reaction Time on the Reaction

TABLE 1.1

The effect of the solvents, catalysts and time on the synthesis of 7-methoxyquinolin-4-ol (P)

| NO. | solvent | T | catalyst | t (h) | product P (%) | isomer I (%) | starting material (%) |
|---|---|---|---|---|---|---|---|
| 1 | xylene | reflux | NP | 22 | 31.5 | 3.8 | 59.6 |
| 2 | xylene | reflux | ZnCl$_2$ (0.1 eq) | 22 | 13.98 | 1.4 | 57.1 |
| 3 | xylene | reflux | ZnCl$_2$ (1.5 eq) | 22 | 12.79 | NP | NP |
| 4 | xylene | reflux | TsOH (0.08 eq) | 22 | NP | NP | 57.4 |
| 5 | xylene | reflux | H$_2$SO$_4$ (0.14 eq) | 22 | NP | NP | 76.7 |
| 6 | DMF | 145° C. | NP | 20 | 0.53 | NP | NP |
| 7 | DMSO | 185° C. | NP | 6 | NP | NP | NP |
| 8 | xylene | reflux | BiCl$_3$ (0.1 eq) | 22 | 1.26 | 0.83 | 70.00 |
| 9 | xylene | reflux | BiCl$_3$ (1.0 eq) | 22 | NP | NP | NP |
| 10 | 1,2,4-tri-methyl-benzene | reflux | NP | 4.5 | 26.79 | 12.40 | 27.78 |
| 11 | 1,2,4-tri-methyl-benzene | reflux | NP | 7.5 | 47.62 | 9.68 | 11.02 |
| 12 | 1,2,4-tri-methyl-benzene | reflux | NP | 15 | 62.94 | 8.49 | 5.72 |
| 13 | 1,2,4-tri-methyl-benzene | 180° C. | NP | 12 | 74.08 | 9.78 | 1.78 |

The % contents are calculated according to the areas of HPLC peaks. NP: not present.

The isomer isolated from the reaction was determined to have the following structure:

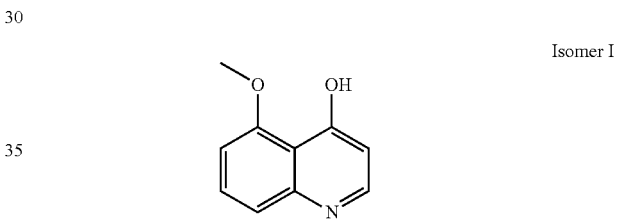

Isomer I

Table 1.1 shows that xylene, DMF and DMSO are not suitable for the reaction. Catalysts ZnCl$_2$, TsOH, H$_2$SO$_4$ and BiCl$_3$ also have no beneficial effect for the reaction. 1,2,4-Trimethylbenzene can be used as the solvent for the reaction, however, the heating at 180° C. for more than 12 hours is needed for the reaction to complete, which is deemed unsuitable for producing the compound on industrial scale.

TABLE 1.2

The effect of ortho-dichlorobenzene (o-DCB) as the solvent on the synthesis of 7-methoxyquinolin-4-ol (P)

| NO. | solvent | T (° C.) | product, isomer & starting material in: | T (h) | product P (%) | isomer I (%) | starting material (%) |
|---|---|---|---|---|---|---|---|
| 1 | o-DCB | 170 | reaction mixture | 5 | 78.64 | 14.75 | 0.40 |
| 2 | o-DCB | 170 | concentrated reaction mixture | 5 | 77.10 | 15.54 | 0.44 |
| 3 | o-DCB | 170 | product mixture after washing with CH$_2$Cl$_2$ | 5 | 83.83 | 14.47 | 0.05 |
| 4 | o-DCB | 170 | product after washing with water | 5 | 98.20 | 0.62 | 0.03 |
| 5 | o-DCB | 170 | the filtrate (water solution) | 5 | 51.46 | 43.45 | 0.02 |

The % contents are calculated according to the areas of HPLC peaks.

TABLE 1.3

The effect of the solvent on the ratio of product P/isomer I

| NO. | solvent | the ratio of product P/isomer I |
|---|---|---|
| 1 | o-DCB (new) | 4.87 |
| 2 | o-DCB (recycled) | 5.12 |
| 3 | o-DCB ((water content >1%) | ND |

ND: not determined

Tables 1.2 and 1.3 show that o-DCB is the most suitable solvent for the cyclization reaction. The recycled o-DCB solvent was as effective as fresh o-DCB and showed minimal effect on the ratio of product P/isomer I. However, water content in o-DCB had significant adverse effect on the reaction, and when o-DCB contained more than 1% of water, the reaction could not complete and dark-colored reaction mixture was obtained.

2. The Optimization of the Molar Reaction Concentration

TABLE 2

The effect of the molar reaction concentration on the ratio of product P/isomer I

| NO. | the molar reaction concentration (M) | t (h) | the ratio of product P/isomer I |
|---|---|---|---|
| 1 | 0.10 | 5 | 5.89 |
| 2 | 0.15 | 5 | 5.06 |
| 3 | 0.20 | 5 | 4.71 |

As indicated in Table 2, the ratio of product P/isomer I was gradually decreased with the increase of the reaction concentration. Considering the product yield, ease of purification and production efficiency, we usually set the reaction concentration at from about 0.10 to about 0.12 M.

3. The Optimization of the Reaction Temperature (T)

TABLE 3

The effect of the reaction temperature (T) on the reaction

| NO. | T (° C.) | t (h) | the transformation rate of the starting material (%) |
|---|---|---|---|
| 1 | 176 | 5 | >99 |
| 2 | 180 | 3 | >99 |

The optimal reaction temperature was at about 180° C.

4. The Optimization of the Purification Process

TABLE 4.1

The effect of the ratio of the weight of the crude product/the volume of dichloromethane on the contents of product P and isomer I

| R* | before or after washing | product P (%) | isomer I (%) |
|---|---|---|---|
| 0.5 | before washing with CH$_2$Cl$_2$ | 77.36 | 14.89 |
| | after washing with CH$_2$Cl$_2$ | 77.66 | 14.90 |
| 0.6 | before washing with CH$_2$Cl$_2$ | 77.72 | 15.18 |
| | after washing with CH$_2$Cl$_2$ | 80.89 | 14.56 |
| 0.7 | before washing with CH$_2$Cl$_2$ | 78.15 | 13.77 |
| | after washing with CH$_2$Cl$_2$ | 81.43 | 14.24 |

R* = $m_{crude\ product}/V_{CH2Cl2}$ (g/mL). The % contents are calculated according to the areas of HPLC peaks.

Experimental results indicated that a high ratio of the weight of the crude product to the volume of CH$_2$Cl$_2$, e.g., R*= or >0.6, resulted in semi-solid that was difficult to stir. Therefore, the optimal ratio of the crude product/CH$_2$Cl$_2$ is R*=$m_{crude\ product}/V_{CH2Cl2}$ (g/mL)=0.5.

TABLE 4.2

The effect of the washing sequence on 7-methoxyquinolin-4-ol (P)

| NO. | purification sequence | | product P (%) | isomer I (%) | weight of product (g) |
|---|---|---|---|---|---|
| 1 | N/A | | 70.93 | 9.77 | 24.70 |
| 2 | first washing with CH$_2$Cl$_2$, followed by water | washing with CH$_2$Cl$_2$ (3 times) | 80.83 | 9.25 | 22.52 |
| | | washing with water (2 times) | 90.66 | 0.51 | 16.78 |
| 3 | first washing with water, followed by CH$_2$Cl$_2$ | washing with water (2 times) | 83.79 | 0.84 | 18.42 |
| | | washing with CH$_2$Cl$_2$ (3 times) | 87.70 | 0.40 | 16.25 |

N/A: not available. The % contents are calculated according to the areas of HPLC peaks.

According to the results described in Table 4.2, the product mixture was best purified by first washing with CH$_2$Cl$_2$ three times, followed by water twice.

TABLE 4.3

The effect of the temperature during filtration

| | NO. | 1 | 2 | 3 | 4 | 5 |
|---|---|---|---|---|---|---|
| | T(° C.) | 50 | 45 | 40 | 35 | 30 |
| product (P) | the product (%) | 96.90 | 91.78 | 94.06 | 96.15 | 96.11 |
| | the impurities (%) | 1.38 | 1.52 | 1.43 | 1.20 | 1.29 |
| | the product weight (g) | 3.12 | 3.12 | 3.19 | 3.30 | 3.36 |
| mother solution | the product (%) | 64.90 | 53.43 | 59.84 | 58.80 | 55.40 |
| | the impurities (%) | 28.14 | 36.17 | 29.82 | 33.73 | 36.50 |
| | the product weight (g) | 1.47 | 1.50 | 1.48 | 1.26 | 1.24 |

The % contents are calculated according to the areas of HPLC peaks.

We also investigated the temperature effect during the filtration in the water washing process. Temperature did not seem to have significant effects on water washing process when T is in the range of from about 30° C. to about 50° C.

What is claimed is:

1. A process for preparing a compound of Formula (I),

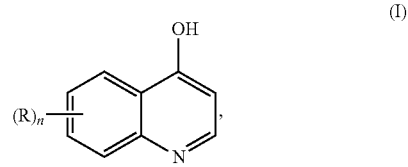

(I)

wherein:
each R is independently F, Cl, Br, I, CN, (C$_1$-C$_6$)alkyl, OR$^a$, or NR$^b$R$^c$;
n is 0, 1, 2, 3, or 4;
each of R$^a$, R$^b$ and R$^c$ is independently H, (C$_1$-C$_6$)alkyl, (C$_3$-C$_6$)cycloalkyl, —(C$_1$-C$_4$)alkylene-(C$_3$-C$_6$)cycloalkyl, 3-6 membered heterocyclyl, —(C$_1$-C$_4$)alkylene-(3-6 membered heterocyclyl), (C$_6$-C$_{10}$)aryl, —(C$_1$-C$_4$)alkylene-(C$_6$-C$_{10}$)aryl, 5-10 membered heteroaryl, or —(C$_1$-C$_4$)alkylene-(5-10 membered heteroaryl), wherein each of the (C$_1$-C$_6$)alkyl, (C$_3$-C$_6$)cycloalkyl, —(C$_1$-C$_4$)alkylene-(C$_3$-C$_6$)cycloalkyl, 3-6 membered heterocyclyl, —(C$_1$-C$_4$)alkylene-(3-6 membered heterocyclyl), (C$_6$-C$_{10}$)aryl, —(C$_1$-C$_4$)alkylene-(C$_6$-C$_{10}$)aryl, 5-10 membered heteroaryl and —(C$_1$-C$_4$)alkylene-(5-10 membered heteroaryl) is optionally substituted with 1, 2, 3, or 4 substitutents independently selected from F, Cl, CN, N₃, OH, (C₁-C₆)alkyl, (C₁-C₆)haloalkyl, and (C₁-C₆)alkoxy;
and wherein the compound of Formula (I) is not one of the following compounds:

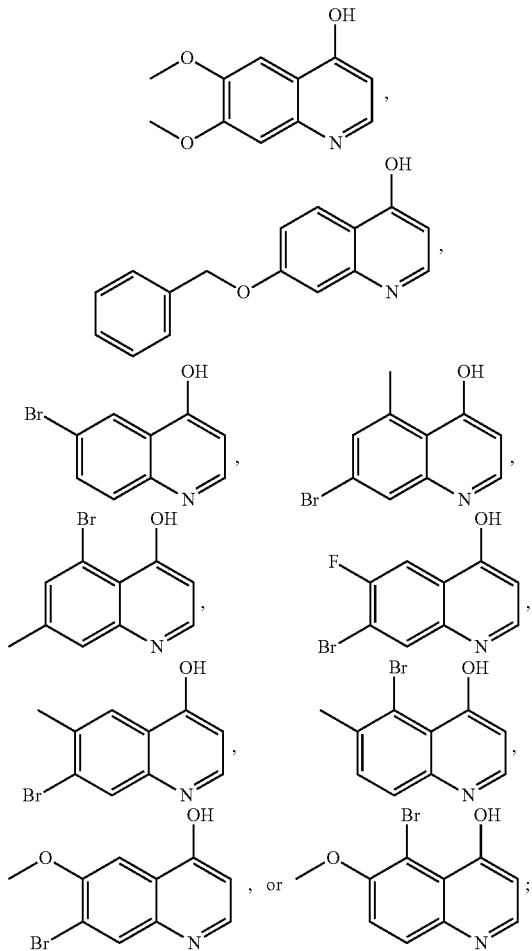

the process comprising:
contacting the compound of Formula (II):

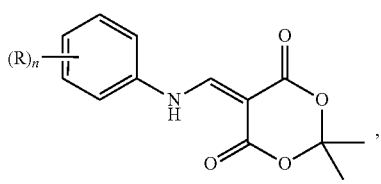

with a dichlorobenzene of Formula (III):

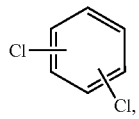

to obtain a reaction mixture containing the compound of Formula (I);
wherein the dichlorobenzene of Formula (III) is

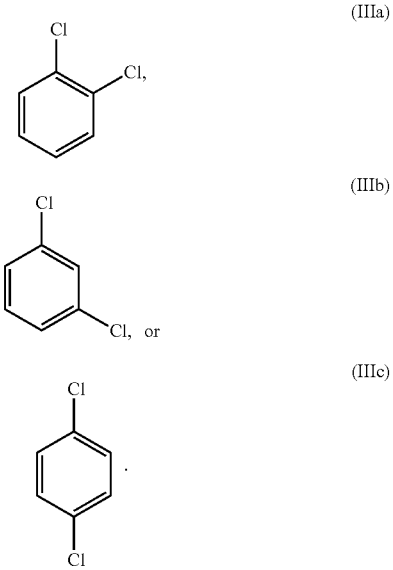

2. The process according to claim 1, wherein each R is independently F, I, CN, methyl, ethyl, n-propyl, i-propyl, n-butyl, i-butyl, t-butyl, OR$^a$, or NR$^b$R$^c$.

3. The process according to claim 1, wherein each of R$^a$, R$^b$ and R$^c$ is independently H, (C₁-C₄)alkyl, (C₅-C₆)cycloalkyl, —(C₁-C₂)alkylene-(C₅-C₆)cycloalkyl, 5-6 membered heterocyclyl, —(C₁-C₂)alkylene-(5-6 membered heterocyclyl), phenyl, —(C₁-C₂)alkylene-phenyl, or 5-6 membered heteroaryl, wherein each of the (C₁-C₄)alkyl, (C₅-C₆)cycloalkyl, —(C₁-C₂)alkylene-(C₅-C₆)cycloalkyl, 5-6 membered heterocyclyl, —(C₁-C₂)alkylene-(5-6 membered heterocyclyl), phenyl, —(C₁-C₂)alkylene-phenyl, and 5-6 membered heteroaryl, is optionally substituted with 1, 2, 3, or 4 substitutents independently selected from F, Cl, CN, N₃, OH, (C₁-C₃)alkyl, and (C₁-C₃)alkoxy.

4. The process according to claim 1, wherein each of R$^a$, R$^b$ and R$^c$ is independently H, methyl, ethyl, n-propyl, i-propyl, n-butyl, i-butyl, or t-butyl.

5. The process according to claim 1, wherein the compound of Formula (I) is compound (Ia),

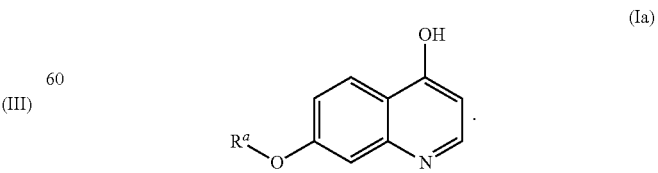

6. The process according to claim 1, wherein the compound of Formula (II) is compound (IIa),

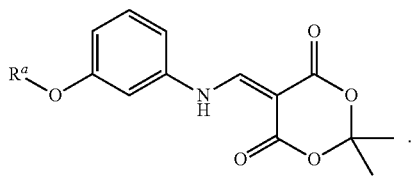
(IIa)

7. The process according to claim 1, wherein the reaction is carried out at a temperature from about 160° C. to about 220° C.

8. The process according to claim 1, wherein the reaction is carried out at a temperature from about 170° C. to about 190° C.

9. The process according to claim 1, wherein the molar concentration of compound of Formula (II) in the dichlorobenzene of Formula (III) is from about 0.05 M to about 0.45 M.

10. The process according to claim 1, wherein the molar concentration of compound of Formula (II) in the dichlorobenzene of Formula (III) is from about 0.10 M to about 0.25 M.

11. The process according to claim 1, further comprising a purification process for purifying the compound of Formula (I), wherein the purification process comprises the steps of:

(a) concentrating the reaction mixture under vacuum to provide a solid;
(b) stirring the solid of step (a) in dichloromethane ($CH_2Cl_2$) to form a mixture;
(c) isolating the solid from the mixture of step (b) by filtration;
(d) stirring the solid of step (c) in water to form an aqueous mixture;
(e) isolating the solid from the aqueous mixture of step (d) by filtration, repeating steps (d) and (e) if needed; and
(f) drying the isolated solid of step (e) to form purified compound of Formula (I).

12. The process according to claim 11, wherein a ratio of the weight (in gram) of the solid obtained in step (a) to the volume (in mL) of $CH_2Cl_2$ used in step (b) is from about 0.4 to about 0.8.

13. The process according to claim 11, wherein a ratio of the weight (in gram) of the solid obtained in step (a) to the volume (in mL) of $CH_2Cl_2$ used in step (b) is from about 0.5 to about 0.7.

14. The process according to claim 11, wherein the mixture in step (b) is stirred at 45° C. for 2 hours.

15. The process according to claim 11, wherein the aqueous mixture in step (d) is stirred at 100° C. for 2 hours.

16. The process according to claim 11, wherein the filtration in step (e) is carried out at a temperature from about 25° C. to about 60° C.

* * * * *